US012558242B2

(12) United States Patent
Bonutti

(10) Patent No.: US 12,558,242 B2
(45) Date of Patent: *Feb. 24, 2026

(54) ANATOMIC NEEDLE SYSTEM

(71) Applicant: P Tech, LLC, Effingham, IL (US)

(72) Inventor: Peter M. Bonutti, Manalapan, FL (US)

(73) Assignee: P TECH, LLC, Manalapan, FL (US)

( * ) Notice: Subject to any disclaimer, the term of this patent is extended or adjusted under 35 U.S.C. 154(b) by 15 days.

This patent is subject to a terminal disclaimer.

(21) Appl. No.: 17/388,471

(22) Filed: Jul. 29, 2021

(65) Prior Publication Data

US 2022/0096255 A1      Mar. 31, 2022

Related U.S. Application Data

(60) Continuation of application No. 14/860,218, filed on Sep. 21, 2015, now Pat. No. 11,096,809, which is a division of application No. 12/707,945, filed on Feb. 18, 2010, now Pat. No. 9,168,163.

(51) Int. Cl.
| | |
|---|---|
| *A61F 2/95* | (2013.01) |
| *A61F 2/958* | (2013.01) |
| *A61M 25/02* | (2006.01) |
| *A61M 25/06* | (2006.01) |

(52) U.S. Cl.
CPC ............... *A61F 2/95* (2013.01); *A61F 2/958* (2013.01); *A61M 25/02* (2013.01); *A61M 25/065* (2013.01); *A61F 2230/0041* (2013.01); *A61F 2250/0018* (2013.01); *A61M 2025/0253* (2013.01); *A61M 2025/028* (2013.01)

(58) Field of Classification Search
CPC .... A61F 2/95; A61F 2/958; A61F 2230/0041; A61M 25/065; A61M 25/02; A61B 2017/3445; A61B 2017/3447; A61B 17/3468; A61B 17/3431
See application file for complete search history.

(56) References Cited

U.S. PATENT DOCUMENTS

| | | | |
|---|---|---|---|
| 2,899,959 | A | 8/1959 | Ginsburg |
| 3,598,118 | A | 8/1971 | Warren |
| 4,518,383 | A | 5/1985 | Evans |
| 4,610,671 | A | 9/1986 | Luther |
| 4,771,776 | A | 9/1988 | Powell et al. |
| 5,569,295 | A | 10/1996 | Lam |

(Continued)

FOREIGN PATENT DOCUMENTS

| | | |
|---|---|---|
| WO | 2008092782 | 8/2008 |

OTHER PUBLICATIONS

International Search Report; PCT/US2011/024003; dated Jun. 20, 2011; 15 pages.

*Primary Examiner* — Thomas Mcevoy
(74) *Attorney, Agent, or Firm* — Stinson LLP

(57) ABSTRACT

A needle system for providing fluidic and/or instrument access to an internal body structure. Exemplary embodiments may include non-linear needles having anatomically appropriate lengths and curvatures. Some exemplary embodiments may include a pivotable base, which may assist in stabilizing the needle system with respect to a body structure and/or may be reconfigurable into a safety guard position. Exemplary needle systems may include expandable conduits providing fluidic and/or instrument pathways into internal body structures.

22 Claims, 20 Drawing Sheets

(56) References Cited

U.S. PATENT DOCUMENTS

| | | | |
|---|---|---|---|
| 5,573,517 A * | 11/1996 | Bonutti | A61B 17/0401 |
| | | | 606/198 |
| 6,019,777 A | 2/2000 | Mackenzie | |
| 6,162,236 A | 12/2000 | Osada | |
| 6,171,282 B1 | 1/2001 | Ragsdale | |
| 7,052,483 B2 | 5/2006 | Wojcik | |
| 7,144,388 B2 | 12/2006 | Crawford | |
| 2003/0171716 A1 | 9/2003 | Ejlersen | |
| 2004/0215307 A1 | 10/2004 | Michels | |
| 2004/0236412 A1 | 11/2004 | Brar | |
| 2005/0113901 A1 | 5/2005 | Coe | |
| 2005/0284815 A1 * | 12/2005 | Sparks | A61M 1/1647 |
| | | | 604/4.01 |
| 2006/0036214 A1 | 2/2006 | Mogensen | |
| 2006/0135981 A1 * | 6/2006 | Lenker | A61M 29/02 |
| | | | 606/191 |
| 2007/0043338 A1 | 2/2007 | Moll et al. | |
| 2008/0039917 A1 | 2/2008 | Cross | |
| 2008/0215008 A1 | 9/2008 | Nance et al. | |
| 2008/0287971 A1 | 11/2008 | Kuntz | |
| 2008/0294103 A1 | 11/2008 | Pereira | |
| 2009/0048563 A1 * | 2/2009 | Ethelfeld et al. | |
| 2009/0131776 A1 * | 5/2009 | Simpson et al. | |
| 2009/0149714 A1 | 6/2009 | Bonadio | |
| 2009/0259143 A1 | 10/2009 | Bakhtyari-Nejad-Esfahani | |
| 2009/0287182 A1 | 11/2009 | Bishop et al. | |
| 2010/0004662 A1 | 1/2010 | Olliver | |
| 2010/0140125 A1 | 6/2010 | Mathiasen | |
| 2011/0190683 A1 | 8/2011 | Gellman et al. | |

* cited by examiner

PLAN VIEW

FRONT ELEVATION VIEW

RIGHT SIDE ELEVATION VIEW

PERPSECTIVE VIEW

300B

302B

50B

ANATOMIC NEEDLE SYSTEM

CROSS REFERENCE TO RELATED APPLICATIONS

This patent application is a divisional application of U.S. patent application Ser. No. 12/707,945, filed Feb. 18, 2010, the entirety of which is incorporated by reference.

BACKGROUND

The present disclosure is directed to needle and/or cannula systems and, more particularly, to needle systems providing access with respect to an internal body structure.

SUMMARY

Exemplary embodiments may include a needle system for providing access with respect to an internal body structure. Exemplary embodiments may move a fluid, substance, implant, and/or instrument into and/or out of the body or any part thereof. Exemplary embodiments may include partially or entirely non-linear needles having anatomically appropriate lengths and curvatures. Some exemplary embodiments may include a pivotable and/or slidable base, which may assist in stabilizing the needle system with respect to a body structure and/or may be reconfigurable into a safety guard position. Exemplary needle systems may include an expandable conduit, needle, and/or cannula which may provide a pathway with respect to an internal body structure.

In an aspect, a needle system may include a housing, and a tubular needle extending distally from the housing, the needle including a substantially straight section extending from the housing and a bent section extending distally and non-linearly from the straight section. A length and/or position of the bent section may be associated with a depth of a biological structure beneath a tissue surface.

In a detailed embodiment, a needle system may include a base coupled to the housing, and the base may include a base surface shaped to engage the tissue surface. In a detailed embodiment, the base surface may include a substantially concave portion or a groove running along its length and adapted to seat upon a convex or protruding feature on the skin (such as a protruding vein). In a detailed embodiment, the base may be pivotably and/or slidably coupled to the housing such that the base is pivotable between a first, tissue engaging position, in which the base surface faces generally away from the housing, and a second safety position in which the base surface faces the needle. In a detailed embodiment, in the second position, the base may at least partially cover the needle.

In a detailed embodiment, at least a portion of the needle and/or cannula may be radially expandable from a first diameter to a second diameter, wherein the second diameter is greater than the first diameter. In a detailed embodiment, the needle and/or cannula may receive an endovascular implant therethrough. In another embodiment, an endovascular implant may be positioned over the expandable needle and/or expandable cannula, thereby allowing the needle and/or cannula to radially expand and place the implant (e.g., a stent) with respect to the internal body structure (e.g., against the inside of an artery).

In a detailed embodiment, the bent section may be angled with respect to the straight section. For example, the bent section may be angled with respect to the straight section at an angle anywhere between 0-90 degrees, such as at about 5-45 degrees in a detailed embodiment, the bent section may be angled with respect to the straight section at about 35-45 degrees. In a detailed embodiment, the bent section may be angled with respect to the straight section at about 15-30 degrees. In a detailed embodiment, the bent section may be angled with respect to the straight section at about 5-15 degrees.

In a detailed embodiment, the bent section may be partially or entirely flexible and/or may have shape memory properties with respect to the straight section, which may allow an angle to vary within a range of about 0-180 degrees. In a detailed embodiment, a portion or all of the bent and/or angled sections may include a shape memory material, which may allow the angle to vary within a range of about 0-180 degrees with a change in temperature and/or by the application of heat. In a detailed embodiment, a portion or all of the bent and/or angled sections may include a segmented tubing or braided structure as used in flexible electrical conduit, which may allow the angle to be adjusted within a range of about 0-180 degrees.

In a detailed embodiment, the length of the bent section may be any length suitable for the desired depth within the body, such as about 1-8 mm. In a detailed embodiment, the length of the bent section may be about 1-3 mm. In a detailed embodiment, the length of the bent section may be about 5-8 mm.

In an aspect, a method of accessing a body structure may include selecting a needle system from among a plurality of needle systems based at least in part upon at least one of a type of a body structure to be accessed, a size of the body structure to be accessed, and a depth of the body structure to be accessed, the needle system including a base and a tubular needle, the tubular needle including a straight section extending distally from a housing pivotably mounted to the base and a bent section extending from the straight section; urging the needle into tissue adjacent the body structure to engage tissue adjacent the body structure with the base; and advancing at least a portion of the needle substantially parallel to the body structure and at least partially into the body structure.

In a detailed embodiment, urging the needle into the tissue may include receiving a convex portion of the tissue against a concave guide portion of the base. In a detailed embodiment, the convex portion of the tissue may include tissue overlying a blood vessel. In a detailed embodiment, advancing the needle substantially parallel to the body structure may include translating the base along the tissue while maintaining contact between the base and the tissue. In a detailed embodiment, advancing the needle substantially parallel to the body structure may include advancing the concave guide portion of the base over the convex portion of tissue. In a detailed embodiment, translating the base along the tissue may include translating the base along tissue overlying a vein in a direction generally parallel with the blood vessel in a detailed embodiment, advancing at least the portion of the needle substantially parallel to the body structure may include advancing the bent section of the needle substantially parallel to the body structure and at least partially into the body structure. In a detailed embodiment, the needle may include a hollow passage extending therethrough for introducing and/or drawing fluids to/from the blood vessel. In a detailed embodiment, the needle may be configured to guide other components thereon into the blood vessel.

In a detailed embodiment, a method may include withdrawing the portion of the needle from the body structure and the tissue; and pivoting the base to lie against the needle. In a detailed embodiment, a method may include, after advancing at least the portion of the needle into the body structure, radially expanding at least the portion of the needle from a first diameter to a second diameter, the second diameter being greater than the first diameter. In a detailed embodiment, expanding at least the portion of the needle may include supplying pressurized fluid to the needle. In a detailed embodiment, the needle may be constructed from an elastically expandable material.

In a detailed embodiment, a method may include instilling a fluid into the body structure via the needle. In a detailed embodiment, the body structure may be a blood vessel.

In a detailed embodiment, a method may include passing an endovascular implant and/or instrument into the body structure via the needle.

In an aspect, a penetrating device system may include a penetrating device including a first section, a second section, a third section, a first bend interposing the first section and the second section, and a second bend interposing the second section and the third section.

In a detailed embodiment, the first section, the second section, and the third section may be substantially coplanar. In a detailed embodiment, at least one of the first section, the second section, and the third section may be non-coplanar with the others of the first section, the second section, and the third section. In a detailed embodiment, the needle may be substantially S-shaped.

In a detailed embodiment, at least one of the first section, the second section, and the third section may include an expandable conduit. In a detailed embodiment, the expandable conduit may be configured around at least a portion of the penetrating device. In a detailed embodiment, the expandable conduit may be configured in a side-by-side arrangement with respect to at least a portion of the penetrating device.

In a detailed embodiment, the penetrating device may include at least one of a guide wire, a substantially solid needle, and a substantially hollow needle.

In an aspect, an expandable placement device may include a guide including a distal section including a distal end, and a proximal section, where the distal section is angled with respect to the proximal section; a conduit disposed around at least a portion of the distal section; and an implant disposed around at least a portion of the conduit disposed around the distal section; where expansion of the conduit is operative to deploy the implant.

In a detailed embodiment, the implant may be disposed around the conduit in a collapsed configuration and/or, when deployed, the implant may be in an expanded configuration.

In a detailed embodiment, the conduit may extend from the distal section to the proximal section. In a detailed embodiment, the conduit may be configured to couple to a supply arranged to provide at least one of air, water, sterile fluid, disinfectant, and a therapeutic substance. In a detailed embodiment, the guide may be substantially rigid.

In a detailed embodiment, the conduit may be tightly configured around the guide.

In a detailed embodiment, the implant may include a stent. In a detailed embodiment, the stent may include at least one of a coronary artery stent, a vascular stent, a peripheral vascular stent, a urinary tract stent, and a urethral stent.

BRIEF DESCRIPTION OF THE DRAWINGS

The detailed description refers to the following figures in which.

DETAILED DESCRIPTION

The present disclosure contemplates that many medical and surgical procedures include accessing patients' blood vessels (e.g., veins and/or arteries) or other internal body structures. For example, blood may be withdrawn from a patient's vein and/or fluids may be instilled into a patient's vein. As another example, a patient's body may be accessed during a minimally invasive procedure, such as placement of a coronary artery stent, vascular stent, peripheral vascular stent, urinary tract stent, or urethral stent, cardiac valve replacement, graft placement, pacemaker installation or removal, vascular repairs, implantation of cells (e.g., stem cells), placement of a growth promoting and/or therapeutic substance, and the like. For example, a coronary artery stent may be placed in a subclavian, innominate, and/or carotid artery. Further, the present disclosure contemplates that many medical and surgical procedures include accessing various organs, vessels, and the like. For example, a lumbar puncture may be performed to access a patient's spinal canal to obtain a sample of a patient's cerebrospinal fluid and/or to inject a pharmaceutical, such as spinal anesthesia. As used herein, "structure" refers to any organ (e.g., stomach, gall bladder), vessel, vein, artery, joint (e.g., knee joint) or the like that may be accessed using methods and apparatus disclosed herein.

Figure 1:
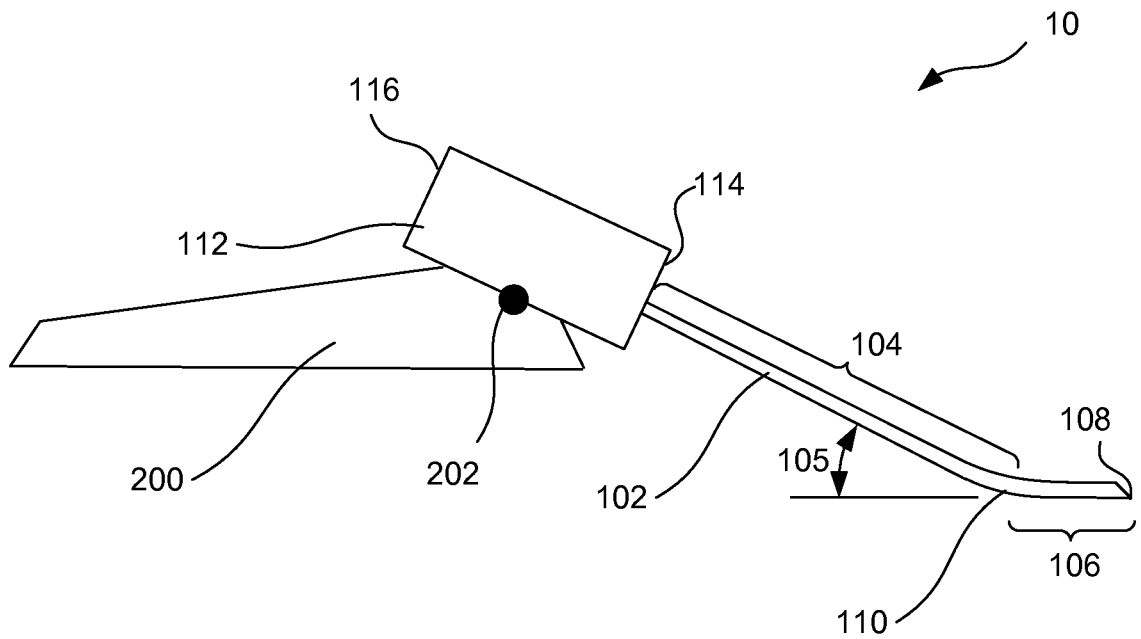
FIG. 1 is a side elevation view of an exemplary needle system.

Referring to FIG. 1, an exemplary needle system 10 may include a needle 102, which may be non-linear. For example, needle 102 may include a first section 104 (also referred to as a straight section) attached to a distal end 114 of a housing 112 and a second section 106 (also referred to as a bent section) which may include a point 108. The first section 104 and the second section 106 may meet at a bend 110. As discussed below, exemplary needle systems 10 may be provided with various angles 105 between the first section 104 and the second section 106 as well as with first sections 104 and second sections 106 of various lengths. Some exemplary needle systems 10 may include flexible needles 102 which may permit angular movement of the first section 104 relative the second section 106. Some exemplary needle systems 10 may include distinct bends 110 between the first section 104 and the second section 106, and some exemplary needle systems 10 may include gradual, curved bends 110 between the first section 104 and the second section 106.

Figure 4:
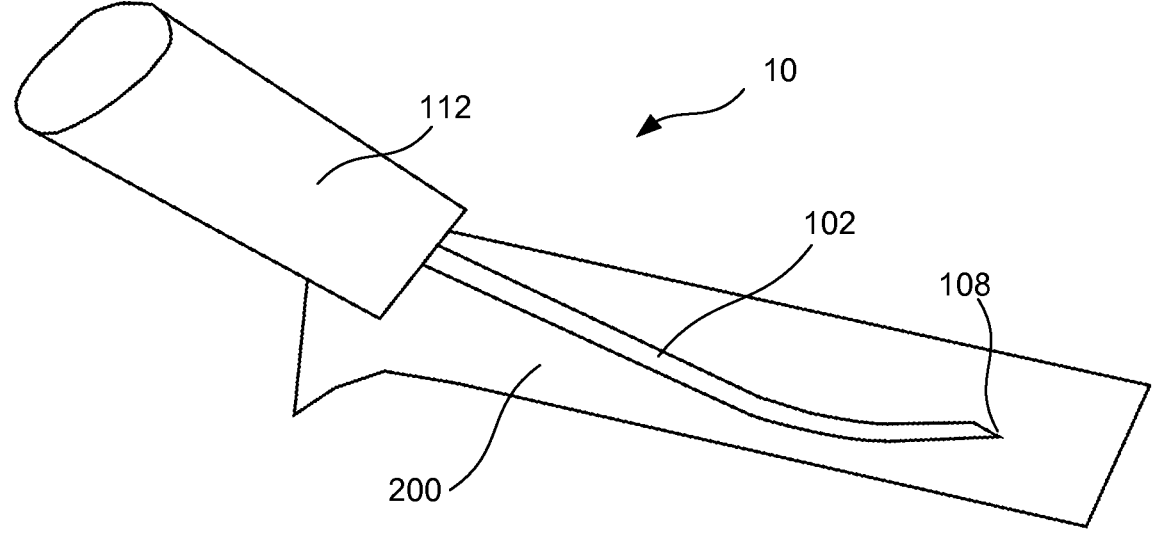
FIG. 4 is a perspective view of an exemplary needle system in which the base is in a safety guard position.

In an exemplary embodiment, housing 112 may include a proximal end 116, which may include a connector for coupling to a conduit for conveying fluids to and/or from the needle 102 and/or a container, such as a tube for collecting a blood sample. A base 200 may be pivotably attached to the housing 112 at a pivot 202. In some exemplary embodiments, base 200 may be constructed from a substantially rigid material, such as molded plastic. In some exemplary embodiments, base 200 may be at least partially flexible and/or deformable. For example, base 200 or a portion thereof may be constructed from a substantially elastic foam material in some exemplary embodiments, the base 200 may be pivotable between a needle-guide position as shown in FIG. 1 and a needle-guard position in which the base covers the needle to protect from accidental needle sticks as shown in FIG. 4. In other exemplary embodiments, the base 200 may be fixed into the needle guide position of FIG. 1.

Figure 2:
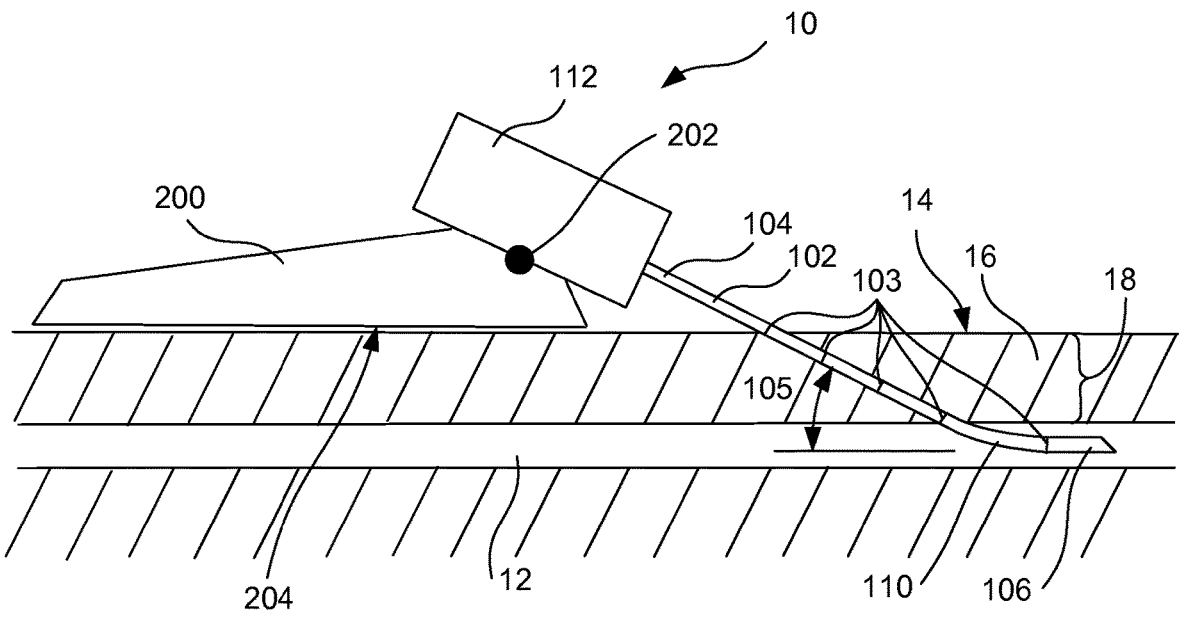
FIG. 2 is a side elevation view of an exemplary needle system installed in a body structure.

Referring to FIG. 2, an exemplary needle system 10 may be used to access a patient's body structure, such as vein 12. When substantially fully inserted, the bent section 106 of the needle 102 may be substantially entirely within the vein 12, and the straight section 104 may extend through the skin surface 14, through the tissue 16 overlaying the vein 12, and into the vein 12. The bend 110 may lie in or near vein 12. A surface 204 of base 200 may contact the skin surface 14 above the vein. In some exemplary embodiments, base 200 may be used to secure the needle 102 in the patient and/or to stabilize the needle 102 relative to the patient. For example, a piece of tape may be used to secure base 200 to the skin surface 14. In some exemplary embodiments, surface 204 may include an adhesive coating for attaching base 200 to skin surface 14 with or without the assistance of tape or other fasteners/retainers. For example and without limitation, the base 200 could be comprised of a soft foam material having an adhesive coating on surface 204, so that the base may be adapted to be fastened to the patient's skin for an extended period of time to retain the needle 102 within the vein or other patient structure. In such an embodiment, the foam material may allow the base to be more comfortably bonded and retained on the skin.

In some exemplary embodiments, a needle system 10 may be configured for use with particular body structures. Referring to FIG. 2, the tissue 16 overlying the vein 12 may have a thickness 18. In an exemplary embodiment, a length of the bent section 106 of the needle 102, a length of the straight section 104 of the needle 102, and/or the angle 105 of the bend 110 may be configured for use on a vein 12 at a particular depth corresponding to thickness 18. For example, the length of the bent section 106 may approximately correspond to the thickness 18 of the tissue 16 overlying the vein 12.

Some exemplary embodiments may include one or more depth indicators configured to allow a surgeon to ascertain the extent of insertion of the needle into a body structure. For example, referring to FIG. 2, exemplary needle 102 may include one or more markings 103 on bent section 106 and/or straight section 104. In addition to or instead of markings 103, some exemplary embodiments may include a depth stop, such as depth stop 102D shown in FIG. 17.

Some exemplary embodiments may be configured to retract needle 102 into housing 112 following use, which may reduce the likelihood of needle-stick injuries. For example, needle 102 may be mounted to housing 112 such that, once it has been withdrawn from the patient, the a spring may displace needle 102 relative to housing 112 such that point 108 is drawn within housing 112.

The present disclosure contemplates that, in adult patients, some veins may be present at about 1-3 mm beneath the skin and that some arteries may be present at about 5-8 mm beneath the skin. Accordingly, some exemplary needle systems 10 may be provided with needles 102 including bent sections 106 having lengths of about 1-8 mm, 1-3 mm for vein access and 5-8 mm for artery access, for example. Some exemplary bend 110 angles 105 may range from about 5 degrees to about 45 degrees. Some exemplary needle systems 10 for accessing shallow structures, such as veins, may include angles 105 of about 5-30 degrees, such as about 5-15 degrees and/or about 15-30 degrees. Some exemplary needle systems 10 for accessing deeper structures, such as arteries, may include angles 105 of about 20-45 degrees. Some bends 110 may have an angular transition, while other bends 110 may have a curved transition. Other exemplary needle systems 10 for accessing other body structures may be configured to access body structures lying about 1-50 mm beneath a surface and, accordingly, may include bent sections about 1-50 mm in length and may include bends having angles of about 1-90 degrees. Some exemplary needle systems 10 configured for accessing even deeper body structures may include longer bent sections. For example, a needle system 10 arranged for cardiovascular use (e.g., stent installation) may include a straight section 104 and/or a bent section 106 about 10 inches long. Such dimensions may be based upon various factors such as, without limitation: structure to be accessed; patient age: patient size, patient obesity; and the like. As another example, some needles 102 according to the present disclosure may be any length including but to not limited to about 1 mm to about 300 mm long.

Some exemplary needles 102 according to the present disclosure may be used to hook around a structure deep within the body and/or to penetrate an internal organ from another side (e.g., a portion of the structure not directly facing the point of entry of the needle 102 into the body/ outer structure). Flexible, deformable, and/or shape memory embodiments described below may also be used in this manner. For example and without limitation, such a device may be configured to access any structure in the body including the spine, the heart, and/or any other organ or part of the cardiovascular system.

Figure 17:
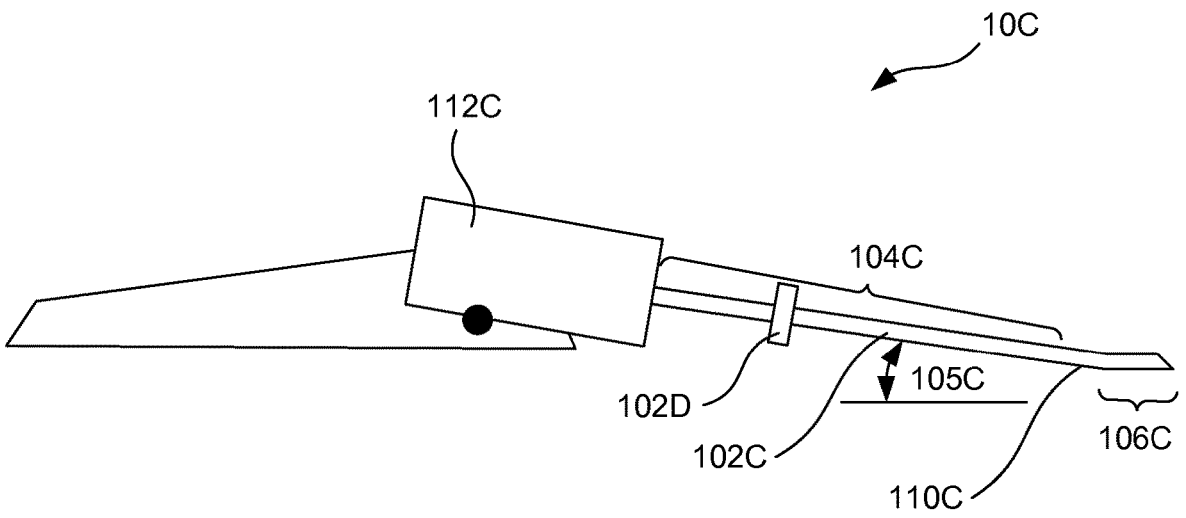
FIG. 17 is a side elevation view of an exemplary needle system including a depth stop.

Referring to FIG. 17, an exemplary needle system 10C may include a needle 102C including a bent section 106C disposed at a shallow angle with respect to a straight section 104C, which may be attached to a housing 112C. The straight section 104C and the bent section 106C may meet at a bend 110C. Angle 105C between the straight section 104C and the bent section 106C may be approximately 5-15 degrees.

In some exemplary embodiments, the base 200 may be angled with respect to the housing 112. For example, the base 200 may be angled with respect to the housing at approximately the angle at which the bent section 106 is angled with respect to the straight section 104. (See, e.g., FIGS. 5 and 6.) In some exemplary embodiments, the base 200 may be angled with respect to the housing 112 at an angle different from the angle at which the bent section 106 is angled with respect to the straight section 104. In some exemplary embodiments, the base 200 may be angled with respect to the housing 112 at about 0-90 degrees. In some more detailed embodiments, the base 200 may be angled with respect to the housing at about 5-45 degrees.

Figure 3:
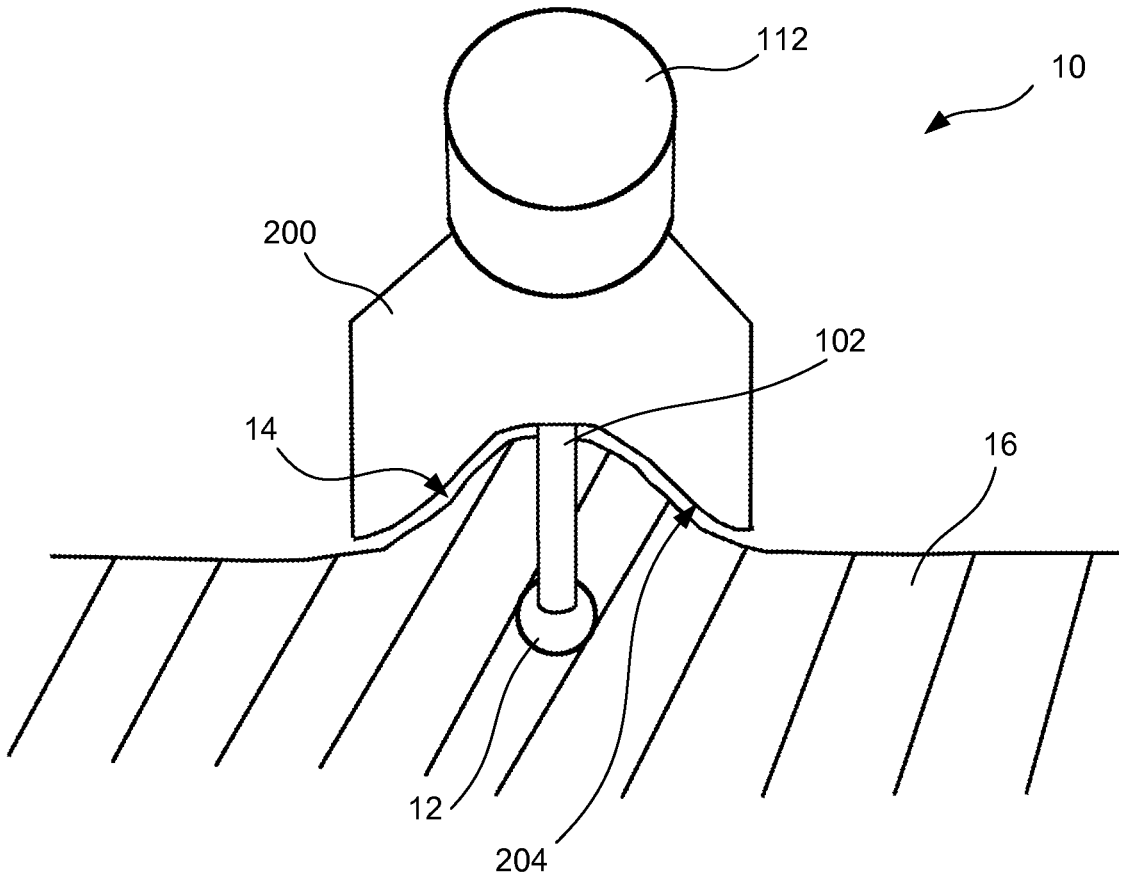
FIG. 3 is a rear elevation view of an exemplary needle system installed in a body structure.

Referring to FIG. 3, in an exemplary needle system 10, the surface 204 of the base 200 may be shaped to receive and be aligned and/or guided upon a portion of the skin surface 14 and/or tissue 16 overlaying the vein 12. For example, surface 204 may have a generally concave shaped groove (or other feature) extending longitudinally thereacross to receive a generally convex portion of skin surface 14 above vein 12. Such an interface between the skin surface 14, tissue 16, and/or the base 200 may assist in placing the needle 10 into the vein 12 (such as by aiding in the alignment of needle 102 with vein 12 and/or preventing movement of the vein 12) and/or may assist in securing the needle 102 and housing 112 subsequent to insertion of the needle 102 into the vein (such as by aiding in minimizing lateral movement of the housing 112 relative to the vein 12). In some exemplary embodiments, base 200 and/or surface 204 may include deformable portions (e.g., foam portions) and/or adhesive portions for interfacing with the skin surface 14. It is contemplated that such protruding vein may be caused by (at least in part) a tourniquet secured at an appropriate spot on the patient's limb, for example, as would be known to those of ordinary skill.

Referring to FIG. 4, in an exemplary needle system 10, the base 200 may be pivotable such that it lies against needle 102 and/or protects point 108, thereby functioning as a safety guard. Base 200 may lock and/or latch into such a configuration, and such a configuration may reduce the risk of accidental needle sticks.

Figure 5:
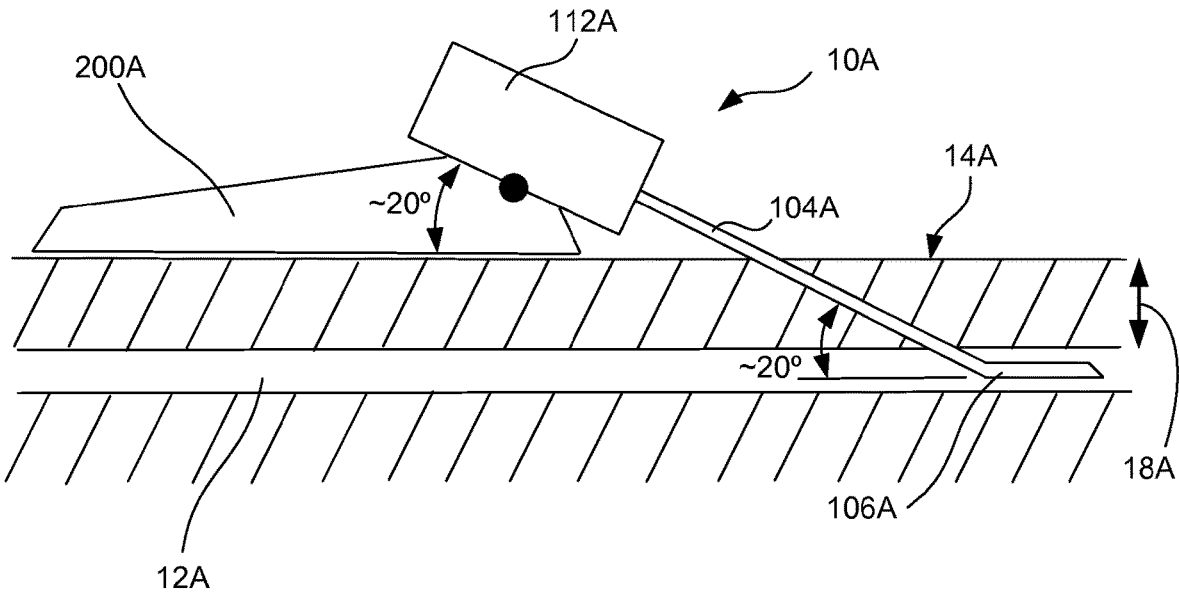
FIG. 5 is a side elevation view of an exemplary needle system installed in a shallow body structure.

Referring to FIG. 5, an exemplary needle system 10A for accessing a shallow structure (such as a vein 12A, which may be at a depth 18A) may include a bent section 106A about 2 mm in length and a straight section 104A angled with respect to bent section 106A at about 20 degrees. If the bent section 106A is approximately parallel with the skin surface 14A, then the straight section 104A may penetrate the skin at about 20 degrees. Straight section 104A may be mounted to a housing 112A, which may be pivotably coupled to a base 200A. In some exemplary needle systems 10A, housing 112A may be angled with respect to base 200A at about 20 degrees when pivoted to a needle-guide position as shown in FIG. 5. In some exemplary embodiments, the angular relationship between housing 112A and base 200A when in the needle-guide position may approximately correspond to the angular relationship between straight section 104A and bent section 106A. Some exemplary needle systems 10A may include straight sections 104A angled with respect to bent sections 106A at about 15-30 degrees. Notably, in this exemplary embodiment, bend 110A includes a distinct change in direction. It is within the scope of the disclosure to utilize an abrupt angular change or a gradual curve in any exemplary embodiment.

Figure 6:
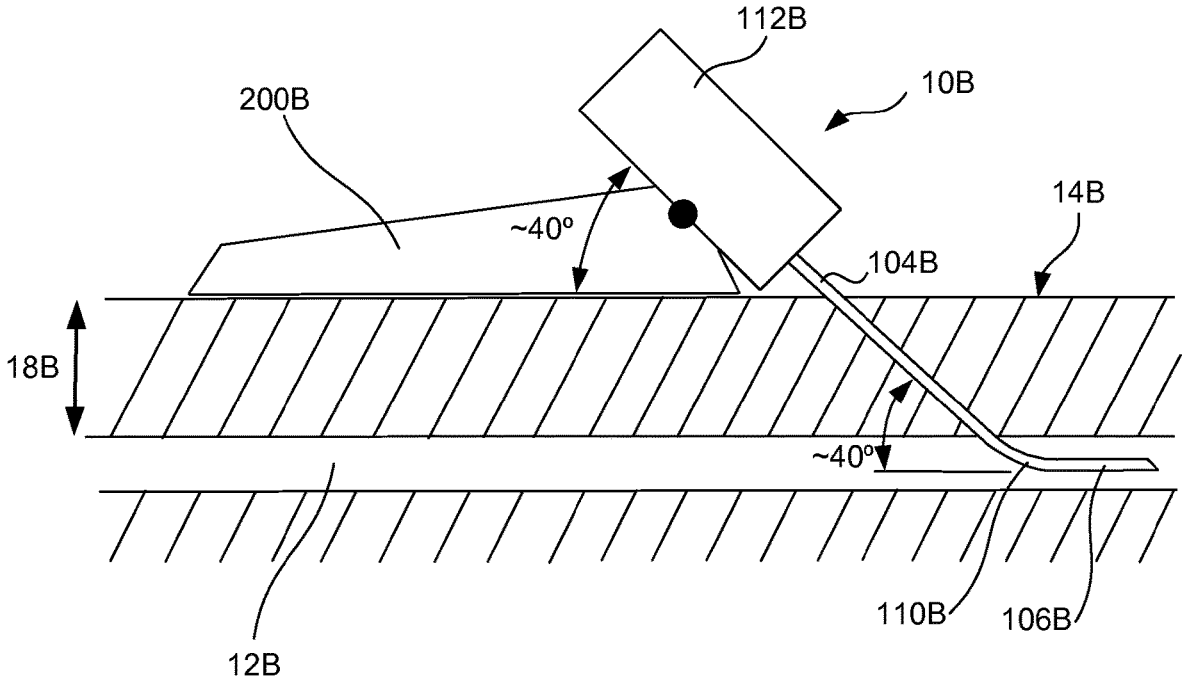
FIG. 6 is a side elevation view of an exemplary needle system installed in a deep body structure.

Referring to FIG. 6, an exemplary needle system 10B for accessing a deep structure (such as an artery 12B, which may be at a depth 18B) may include a bent section 106B about 6 mm in length and a straight section 104B angled with respect to bent section 106B at about 40 degrees. Notably, in this exemplary embodiment, bend 110B includes a gradual curve as opposed to an abrupt angular change. It is within the scope of the disclosure to utilize an abrupt angular change or a gradual curve in any exemplary embodiment. If the bent section 106B is approximately parallel with the skin surface 14B, then the straight section 104B may penetrate the skin at about 40 degrees. Straight section 104B may be mounted to a housing 112B, which may be pivotably coupled to a base 200B. In some exemplary needle systems JOB, housing 112B may be angled with respect to base 200B at about 40 degrees in the needle-guide position as shown in FIG. 6. In some exemplary embodiments, the angular relationship between housing 112B and base 200B may approximately correspond to the angular relationship between straight section 104B and bent section 106B. Some exemplary needle systems 10B may include straight sections 104B angled with respect to bent sections 106B at about 35-45 degrees.

Figure 7:
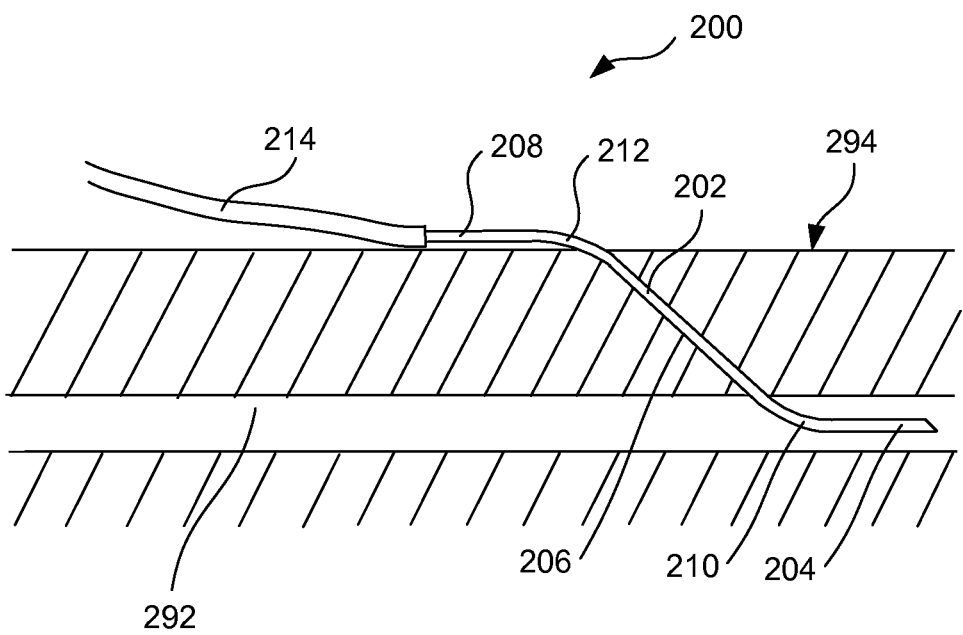
FIG. 7 is a side elevation view of an exemplary needle including two bends.
Figure 8A:
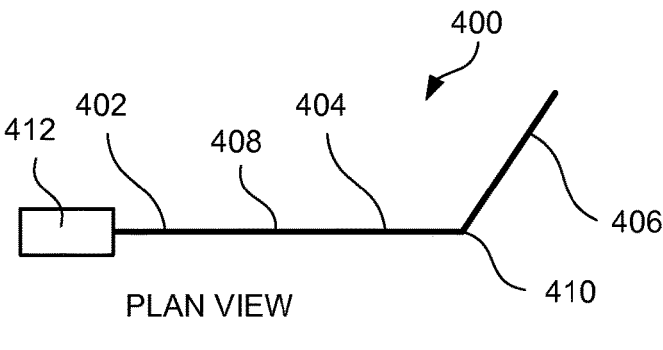
FIG. 8A is a plan view of an exemplary needle including two non-planar bends.
Figure 8B:
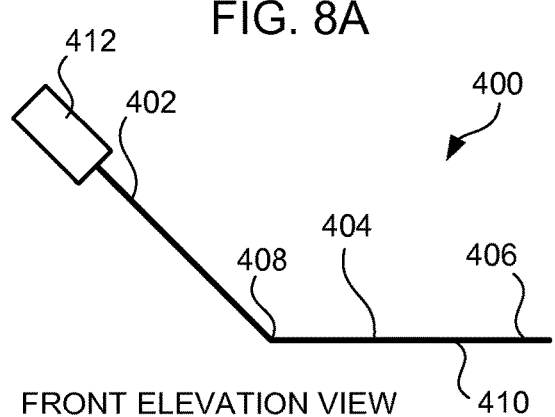
FIG. 8B is a front elevation view of an exemplary needle including two non-planar bends.
Figure 8C:
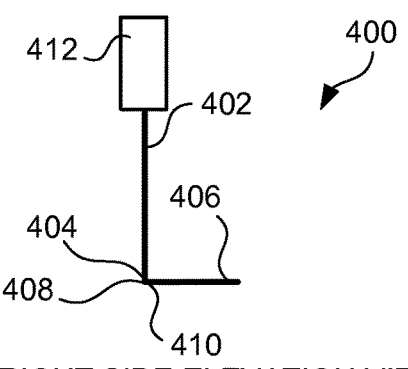
FIG. 8C is a right side elevation view of an exemplary needle including two non-planar bends.
Figure 8D:
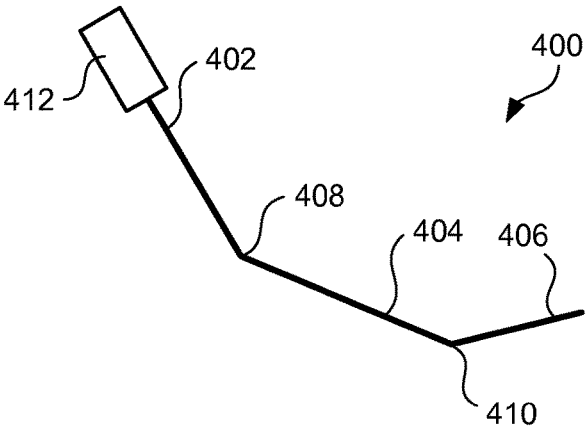
FIG. 8D is a perspective view of an exemplary needle including two non-planar bends.

Referring to FIG. 7, an exemplary needle system 200 may include a needle having more than one curve, such as generally S-shaped needle 202, which may include a first section 204, a second section 206, a third section 208, a first bend 210 interposing the first section 204 and the second section 206, and/or a second bend 212 interposing the second section 206 and the third section 208. In some exemplary embodiments, the needle 202 may be coupled to conduit and/or housing 214, and, in some exemplary embodiments, the needle system 200 may include a housing as described above. Some exemplary needle systems 200 may be utilized to access a body structure 292 lying beneath a surface 294 such that the first section 204 is substantially parallel with the body structure 292 and/or the third section 208 is substantially parallel with the surface 294. In some exemplary embodiments, third section 208 may be secured to the surface 294 (e.g., using tape, adhesive, a resilient band, or some other method). In some exemplary embodiments, the needle sections 204, 206, 208 may lie substantially in the same plane.

In some exemplary embodiments, some needle sections may be non-planar. For example, FIGS. 8A-8D illustrate an alternative exemplary needle 400 which may include more than one curve 408, 410 such that the needle sections 402, 404, 406 are non-coplanar. Such a needle may be used to access a femoral artery, for example, or any other body structure for which it may be useful to penetrate a surface and/or change direction. In some exemplary embodiments, needle 400 may include a housing 412 (which may receive a conduit, a collection container, etc.) and/or needle 400 may be coupled to a conduit as described above.

Figure 9A:
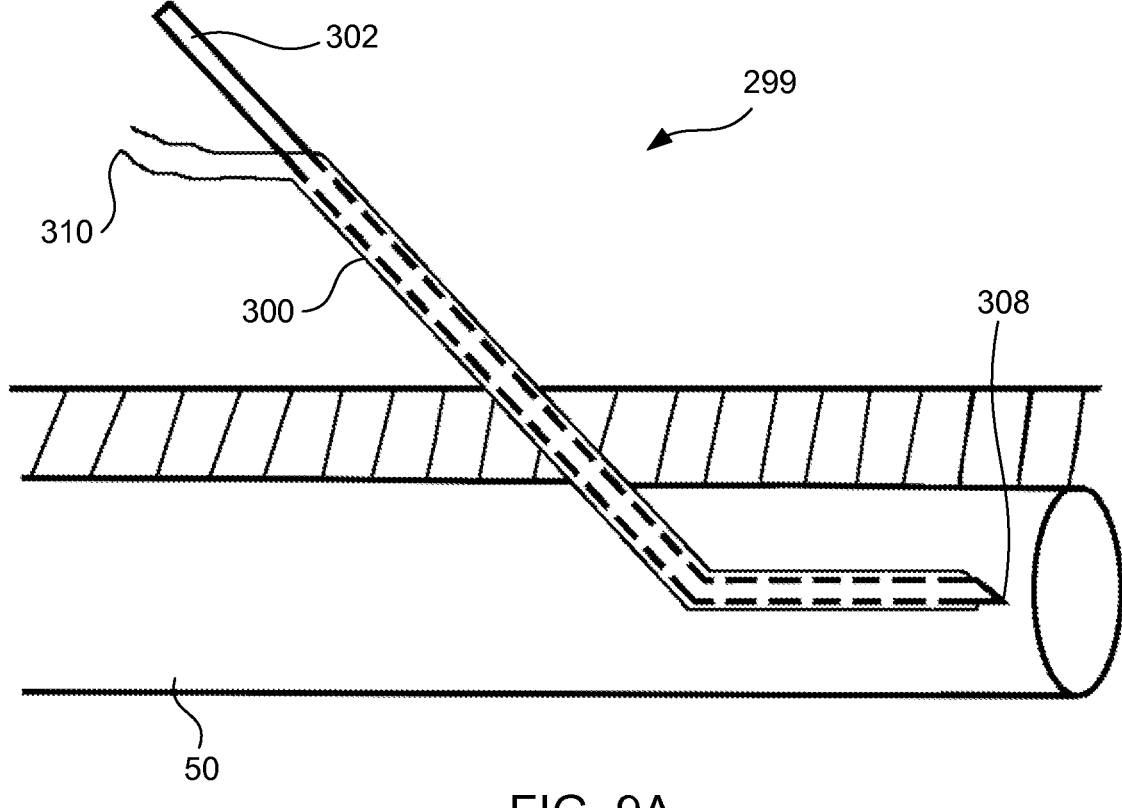
FIG. 9A is an elevation view of an exemplary needle system including a concentrically arranged conduit in a collapsed configuration.

Referring to FIG. 9A, an exemplary expandable access device 299 may include a substantially collapsed conduit 300 affixed to a substantially rigid guide 302, such as a guide wire, a stylet, and/or a needle (or any other penetrating device), which may include a distal end 308. In some exemplary embodiments, guide 302 may include solid and/or hollow portions. A proximal end 310 of the conduit 300 may be configured to couple with a sensor, monitoring system, vacuum, and/or supply for air, water, sterile fluid, disinfectant, and/or a therapeutic substance. Exemplary therapeutic substances may include antibiotics, hydroxypatite, anti-inflammatory agents, steroids, antibiotics, analgesic agents, chemotherapeutic agents, bone morphogenetic protein (BMP), demineralized bone matrix, collagen, growth factors, autogenetic bone marrow, progenitor cells, calcium sulfate, immuno suppressants, fibrin, osteoinductive materials, apatite compositions, germicides, fetal cells, stem cells, enzymes, proteins, hormones, cell therapy substances, gene therapy substances, and/or combinations thereof. In an exemplary embodiment, conduit 300 may be tightly configured around guide 302 during insertion of the access device 299 into a body structure 50, such as a vein, an artery, etc.

Figure 9B:
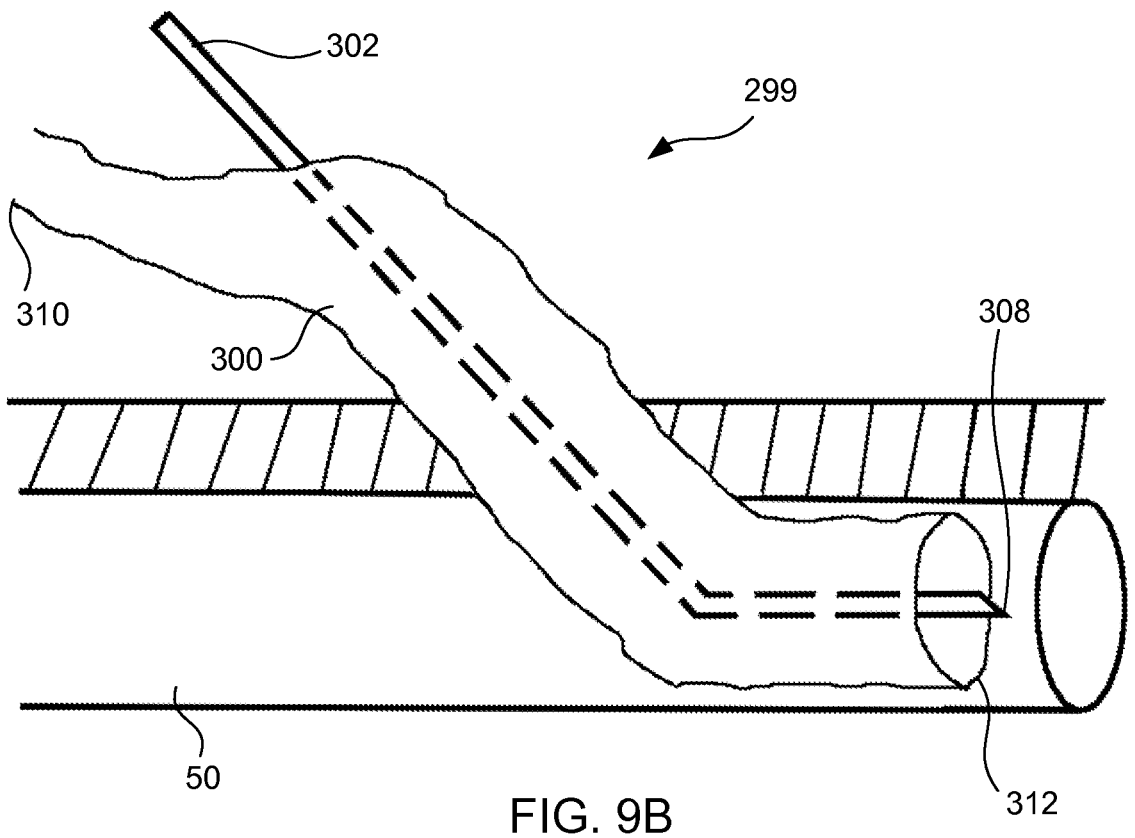
FIG. 9B is an elevation view of an exemplary needle system including a concentrically arranged conduit in an expanded configuration.

Referring to FIG. 9B, the conduit 300 may be expanded to provide a lumen extending from the proximal end 310 of the conduit 300 into the body structure via the distal end 312 of the conduit. In some exemplary embodiments, the conduit 300 may be expanded by application of internal pressure. For example, a fluid, such as saline solution, may be supplied to the collapsed conduit 300 at a pressure greater than the internal pressure of the body lumen 50. This may cause the conduit to expand radially, such that the effective diameter 306 of the conduit increases. In some exemplary embodiments, the conduit 300 may be constructed of materials which remain substantially pliable, and the conduit 300 may at least partially decrease in size when a pressurized fluid is no longer provided.

The distal end 312 of the conduit 300 may include an opening to allow fluid flow and/or instrument access through the conduit 300 to and/or from the body structure 50.

Figure 10A:
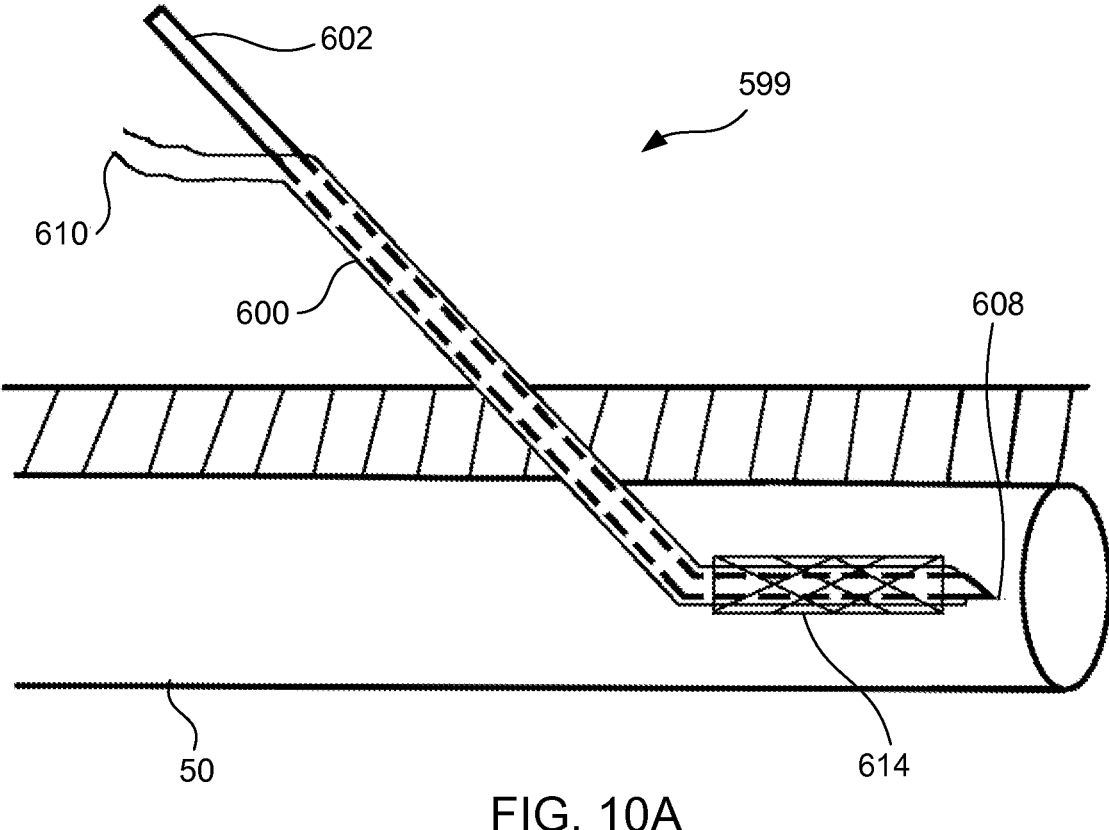
FIG. 10A is an elevation view of an exemplary needle system including a concentrically arranged stent in a collapsed configuration.

Referring to FIG. 10A, an exemplary expandable placement device 599 may be generally similar to expandable access device 299 of FIGS. 9A and 9B. Exemplary expandable placement device 599 may include a substantially collapsed conduit 600 affixed to a substantially rigid guide 602, such as a guide wire, a stylet, and/or a needle (or any other penetrating device), which may include a distal end 608. In some exemplary embodiments, guide 602 may include solid and/or hollow portions. A proximal end 610 of the conduit 600 may be configured to couple with a sensor, monitoring system, vacuum, and/or supply for air, water, sterile fluid, disinfectant, and/or a therapeutic substance. In an exemplary embodiment, conduit 600 may be tightly configured around guide 602 during insertion of the placement device 599 into a body structure 50, such as a vein, an artery, etc. An implant, such as a stent 614 (e.g., a coronary artery stent, vascular stent, peripheral vascular stent, urinary tract stent, and/or urethral stent), may be disposed on conduit 600 in a collapsed configuration.

Figure 10B:
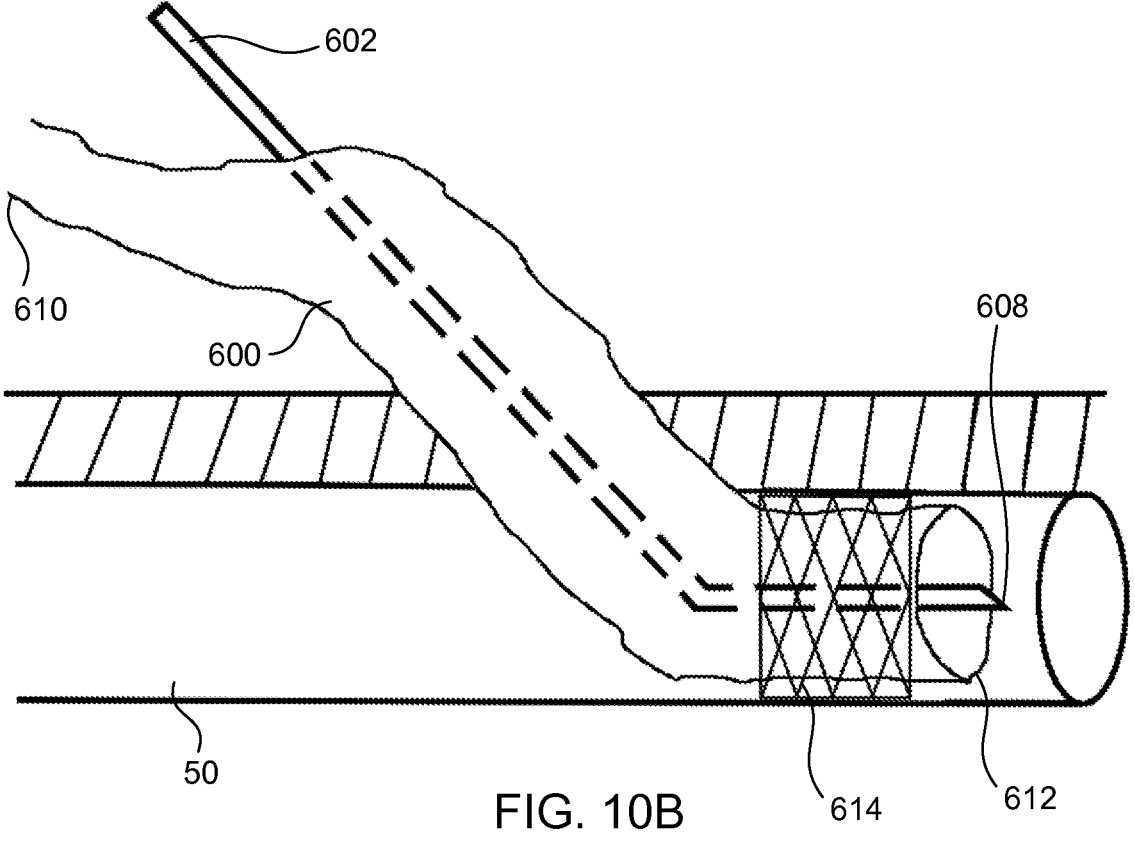
FIG. 10B is an elevation view of an exemplary needle system including a concentrically arranged stent in an expanded configuration.

Referring to FIG. 10B, the conduit 600 may be expanded. In some exemplary embodiments, the conduit 600 may be expanded by application of internal pressure. For example, a fluid, such as saline solution, may be supplied to the collapsed conduit 600 at a pressure greater than the internal pressure of the body lumen 50. This may cause the conduit to expand radially, such that the effective diameter 606 of the conduit increases. In some exemplary embodiments, the conduit 600 may be constructed of materials which remain substantially pliable, and the conduit 600 may at least partially decrease in size when a pressurized fluid is no longer provided. Expansion of conduit 600 may cause expansion of stent 614. For example, stent 612 may be expanded within an artery proximate a plaque accumulation to widen the artery, which may provide increased blood flow past the plaque accumulation.

In some exemplary embodiments, the distal end 612 of the conduit 600 may include an opening to allow fluid flow and/or instrument access through the conduit 600 to and/or from the body structure 50.

Figure 11:
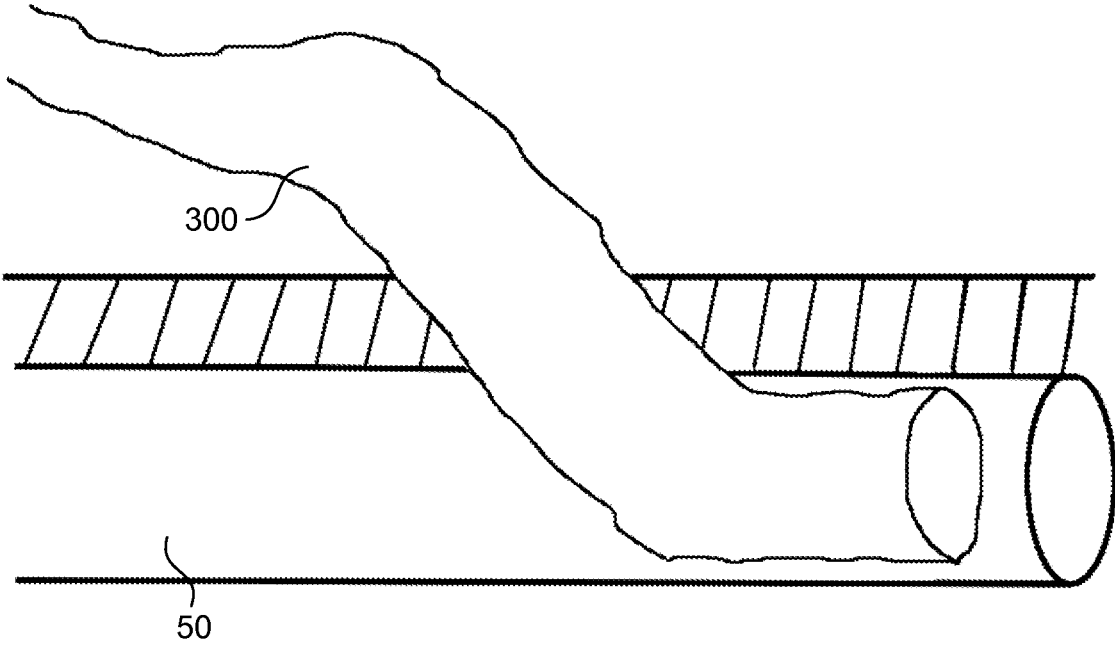
FIG. 11 is an elevation view of an exemplary conduit with the needle removed.
Figure 12:
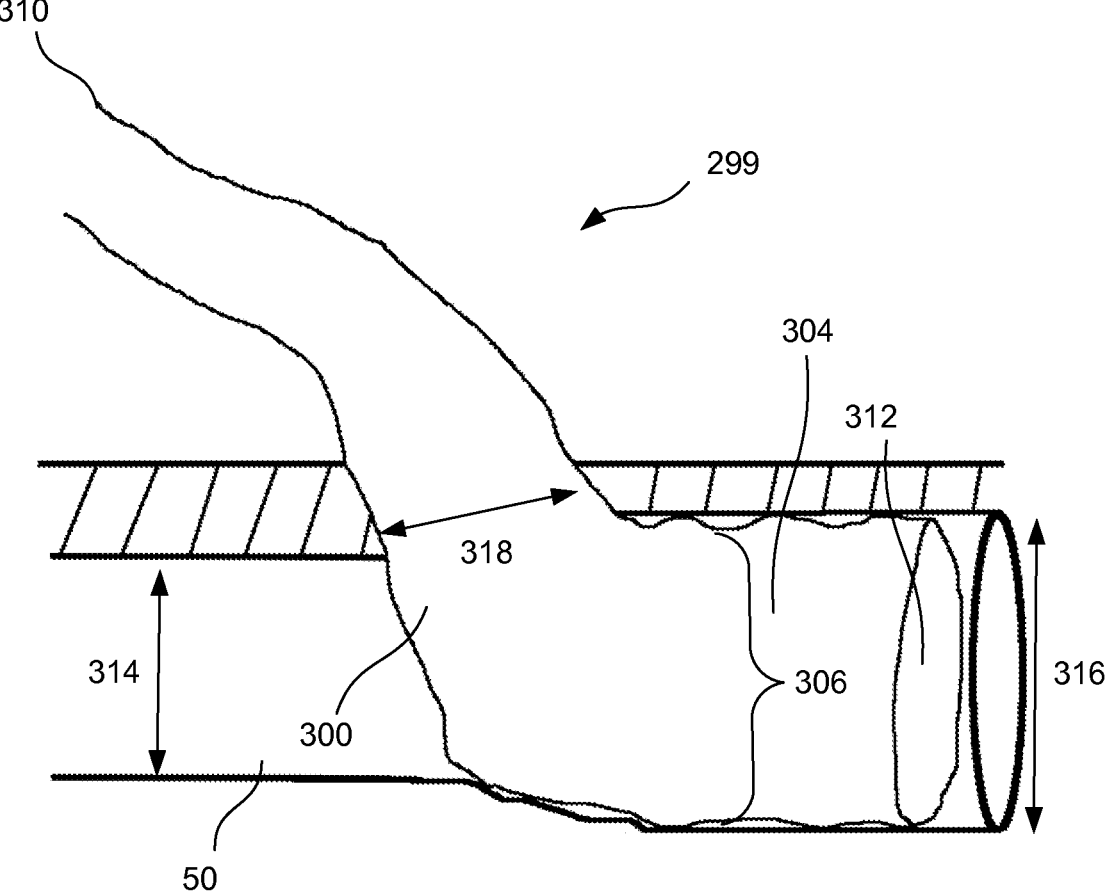
FIG. 12 is an elevation view of an exemplary conduit expanding a body structure.

Referring to FIG. 11, in some exemplary embodiments, the guide 302 may be removed, leaving the conduit 300 as an access to the body structure 50.

Figure 13:
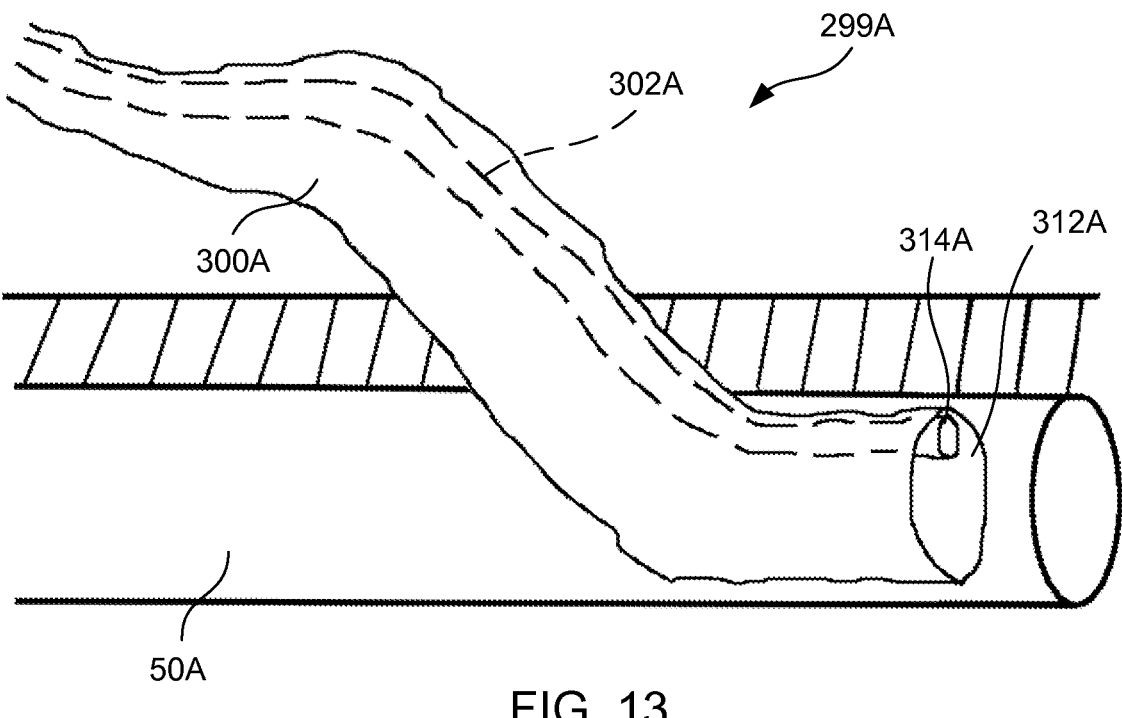
FIG. 13 is an exemplary conduit including an auxiliary lumen arranged within a main lumen.

Referring to FIG. 13, in some exemplary embodiments, the conduit 300 may be expanded to a diameter 306 greater than the initial diameter 314 of the body structure 50. Such expansion of the conduit 300 may enlarge a portion of the body structure 50 to a larger diameter 316, which may permit infusion of fluids at a greater rate than would otherwise be possible. Also, enlargement of the body lumen 50 may permit infusion of viscous fluids, such as blood, into structures 50 that would not normally be suitable for such infusions due to their small size. The enlargement of the body structure 50 may be temporary or permanent. In some exemplary embodiments, the skin (or other body surface) penetration may be enlarged to greater diameter 318 as the conduit 300 is expanded.

Some exemplary embodiments may be configured to permit outflow of fluid through the conduit 300. For example, some exemplary embodiments may be used to obtain blood samples by drawing blood from the vein, through the conduit 300, and into a sample container.

An exemplary conduit 300 may be expandable, for example to about 2-10 mm. Some exemplary embodiments may be used to provide a variable diameter access. For example, conduit 300 may be installed in a vein and expanded to about 2 mm for its planned use. If circumstances requiring a larger access arise (e.g., a medical emergency requiring rapid infusion of fluids), the conduit may be expanded to 5 mm, for example. In some exemplary embodiments, once the higher flow causing the expansion is reduced, the conduit 300 may contract to a smaller diameter. Thus, some exemplary embodiments may provide variable size conduits 300 that may be expanded and/or contracted as needed. In addition, even if a use requiring a larger diameter is not anticipated, utilizing an expandable conduit 300 may prevent the need to quickly place a separate, larger diameter intravenous line in a situation urgently requiring a large diameter intravenous access.

In some exemplary embodiments, conduit 300 in the collapsed configuration may conform tightly to the guide 302. For example, in some exemplary embodiments, the collapsed conduit 300 may increase the diameter of the guide 302 by about 1-2 mm.

Figure 14:
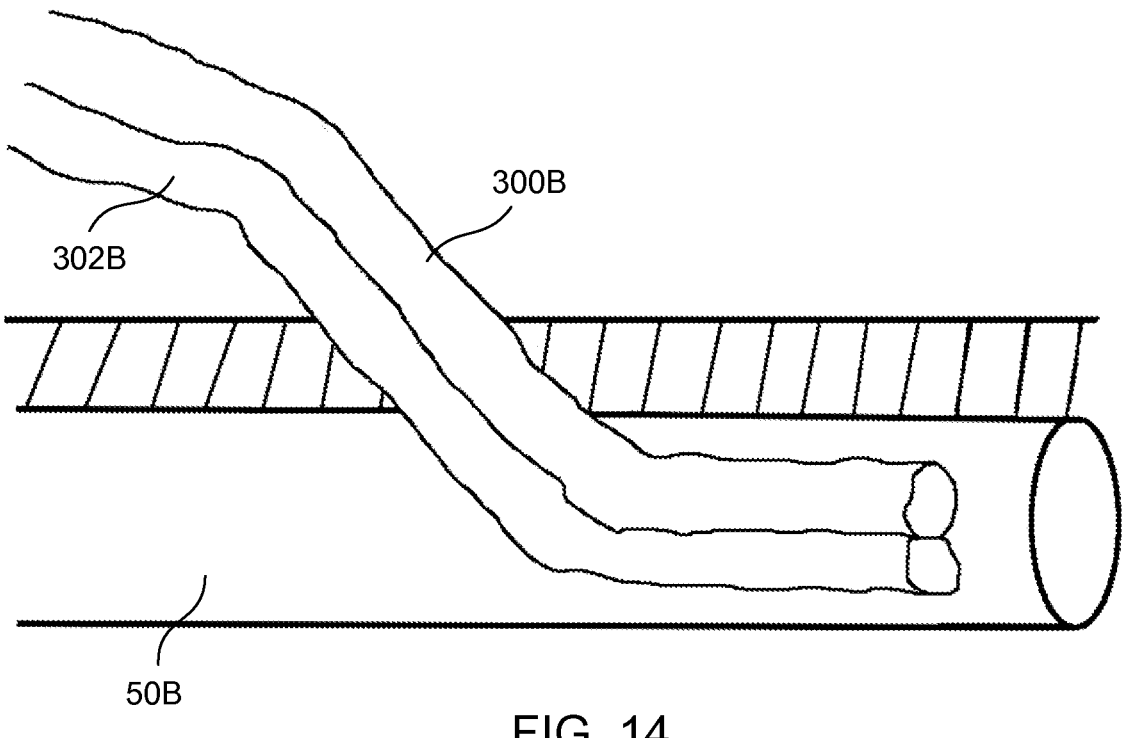
FIG. 14 is an exemplary conduit including main and auxiliary lumens in a side-by-side arrangement.

Some exemplary conduits may include more than one lumen. For example, referring to FIG. 13, an exemplary conduit 300A may include an auxiliary conduit 302A providing an auxiliary lumen within the main conduit 300A. The main conduit 300A and/or the auxiliary conduit 302A may include a distal end 312A, 314A, which may include an opening in fluid communication with the interior of body structure 50A. The main conduit 300A and/or the auxiliary conduit 302A may be utilized to infuse fluids, withdraw fluids, and/or to provide access for surgical instruments. FIG. 14 illustrates an alternative exemplary embodiment including side-by-side conduits 300B, 302B, which may be used to access a body structure 50B.

Figure 15:
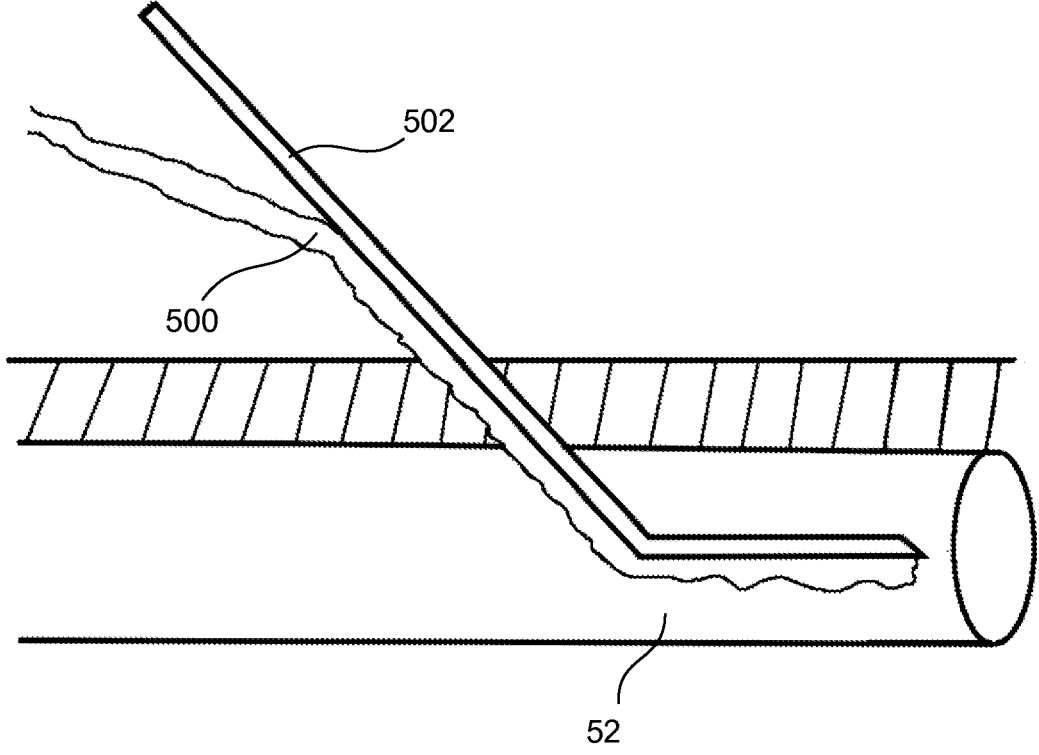
FIG. 15 is an exemplary needle system including a conduit and a needle in a side-by-side arrangement.
Figure 16:
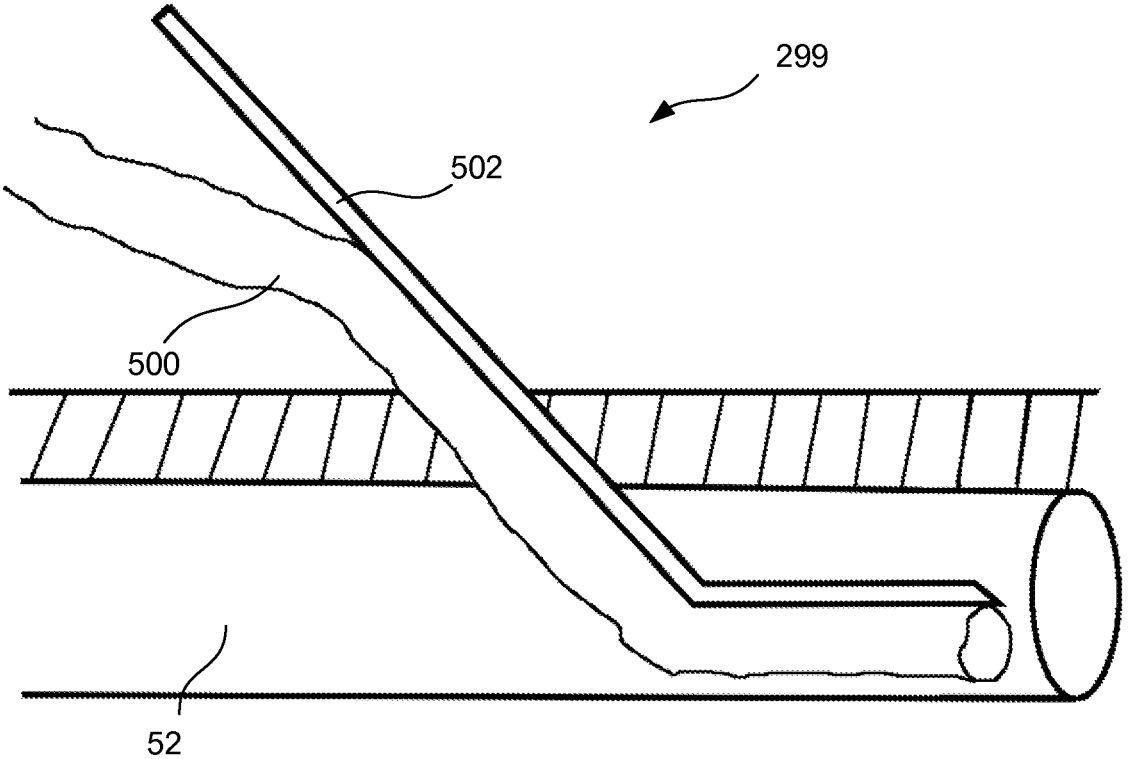
FIG. 16 is an exemplary needle system including a conduit and a needle in a side-by-side arrangement with the conduit expanded; all in accordance with at least some aspects of the present disclosure.

FIG. 15 illustrates an alternative exemplary embodiment in which an expandable conduit 500 is affixed in a side-by-side relationship with guide 502. As illustrated in FIG. 16, the conduit 500 may be expanded to provide a pathway to and/or from body structure 52. Some exemplary embodiments may permit removal of the guide 502 subsequent to installation and/or some exemplary embodiments may include multiple lumens as discussed above.

In some exemplary embodiments, the conduit may be partially or entirely constructed of rubber, elastic, plastic, thermoplastic, and/or any combination thereof. As an example, the conduit may be configured as an elongate tubular member and/or a balloon. As another example, the conduit may be heat-shrinked to conform to the guide/needle for insertion into the body and expand with air and/or fluid pressure in the conduit.

In some exemplary embodiments, a needle and/or guide may be manipulated by a surgeon prior to insertion. For example, an exemplary needle may include a plastically deformable portion, and a surgeon may form the needle (e.g., using a bending iron) into a desired shape prior to use.

In some exemplary embodiments, a kit comprising a plurality of sizes and/or shapes of needles, guides, and/or cannulas may be provided, and a surgeon may select an appropriate needle, guide, and/or cannula based upon an anticipated use and/or the patient's particular characteristics.

Exemplary methods and apparatus discussed herein may be utilized for any procedure requiring installation of a needle and/or cannula into an internal body structure. Exemplary devices and methods may be utilized in percutaneous procedures as well as open surgical procedures involving insertion of a needle and/or cannula into an internal structure.

For example, exemplary needles, guides, and/or conduits described herein may be employed to provide access to vessels for a vascular repair procedure. For example, in an exemplary vascular repair procedure, balloons may be utilized to manipulate and/or stabilize portions of a vessel on each side of an area requiring repair. The balloons may be moved together such that vessel portions are substantially aligned. The vessel portions may be joined circumferentially, such as by suturing, heat sealing, and/or using adhesive. Upon completion of the repair, the balloons and/or the needles, guides, and/or conduits may be removed. These and other processes that may benefit from use of the inventions disclosed herein are described in detail in U.S. Patent Application Publication No. 2008/0065140, the disclosure of which is incorporated by reference.

It is contemplated that devices and methods disclosed herein may be applied using minimally invasive incisions and techniques to fasten muscles, tendons, ligaments, bones, nerves, and blood vessels. A small incision(s) may be made adjacent the damaged tissue area to be repaired, and a tube, delivery catheter, sheath, cannula, and/or expandable cannula may be used to perform the methods according to the present disclosure.

U.S. Pat. No. 5,320,611 entitled "Expandable Cannula Having Longitudinal Wire and Method of Use" discloses cannulas for surgical and medical use which may be expandable along their lengths. The cannulas may be inserted through tissue when in an unexpanded condition and with a small diameter. The cannulas are then expanded radially outwardly to give a fullsize instrument passage. The cannulas may be asymmetrically expandable to allow the passage of asymmetrically or irregularly shaped devices, implants, and/or instruments. Expansion of the cannulas may occur against the viscoelastic resistance of the surrounding tissue. The expandable cannulas may not require an incision and/or may be self-introducing, thereby making only a small or needle-sized opening in the tissue.

U.S. Pat. Nos. 5,674,240; 5,961,499; and 6,338,730 also disclose cannulas for surgical and medical use which may be expandable along a portion of or their entire lengths. The cannula can be provided with a pointed end portion and can include wires having cores which are enclosed by jackets. The jackets may be integrally formed as one piece with a sheath of the cannula. The cannula may be expanded by inserting members and/or by fluid pressure. An expandable chamber may be provided at the distal end of the cannula.

Furthermore, any of the aforementioned embodiments may be used in conjunction with indirect visualization, such as endoscopic guidance, computer assisted navigation, magnetic resonance imaging, CT scan, ultrasound, fluoroscopy, X-ray, and/or other suitable visualization technique. Some exemplary embodiments may include a radiopaque material for enhancing indirect visualization U.S. Pat. Nos. 5,329, 924; 5,349,956, and 5,542,423 disclose apparatus and methods for use in medical imaging. Also, methods according to the present disclosure may be performed using robotics, such as haptic arms or similar apparatus.

Exemplary embodiments according to the present disclosure may also be utilized with minimally invasive surgery techniques disclosed in U.S. Patent Application Publication No. 2008/0147075. This patent documents discloses, inter alia, apparatus and methods for minimally invasive joint replacement. Furthermore, the methods and devices disclosed therein may be utilized for repairing, reconstructing, augmenting, and/or securing tissue and/or implants during and "on the way out" of a joint replacement procedure.

As another example, it is contemplated that exemplary embodiments disclosed herein may be used in conjunction with the devices and methods disclosed in U.S. Pat. No. 6,820,614 entitled "Tracheal Intubation", which discusses, inter alia, tracheal intubation, positioning apparatus, and magnets in conjunction with a tubular guide member and/or tracheal tube. Additional concepts disclosed are disclosed in U.S. Patent Application Publication Nos. 2008/0086072 entitled "Methods and Devices for Controlling Biologic Microenvironments" and 2008/0306324 entitled "Magnetic Joint Implant".

In some exemplary embodiments, needles and/or guides may be at least partially constructed from one or more biocompatible metals, including stainless steel, nitinol, shape metal alloy, tantalum, porous tantalum, titanium, cobalt-chrome alloys, and/or other metals such as are known to those skilled in the art.

Some exemplary embodiments may include shape-memory alloys such as nickel titanium (NiTi or Nitinol). Other exemplary shape-memory alloys may include CuSn, InTi, TiNi, and/or MnCu Objects made from exemplary shape-memory alloys may be substantially plastically deformed, but may return to their original shape upon a change in temperature and/or the application of heat. In some exemplary embodiments, a needle and/or guide may be constructed of a shape-memory alloy, which may permit the shape of the needle and/or guide to change after insertion into a patient. Some exemplary embodiments may utilize laminated materials having different coefficients of thermal expansion to provide a similar thermally activated shape change effect. Some exemplary embodiments may utilize materials which change shape in response to application of an electric charge. Any material providing shape-change capabilities may be utilized to steer a needle and/or guide during and/or following insertion into a body structure.

Figure 18A:
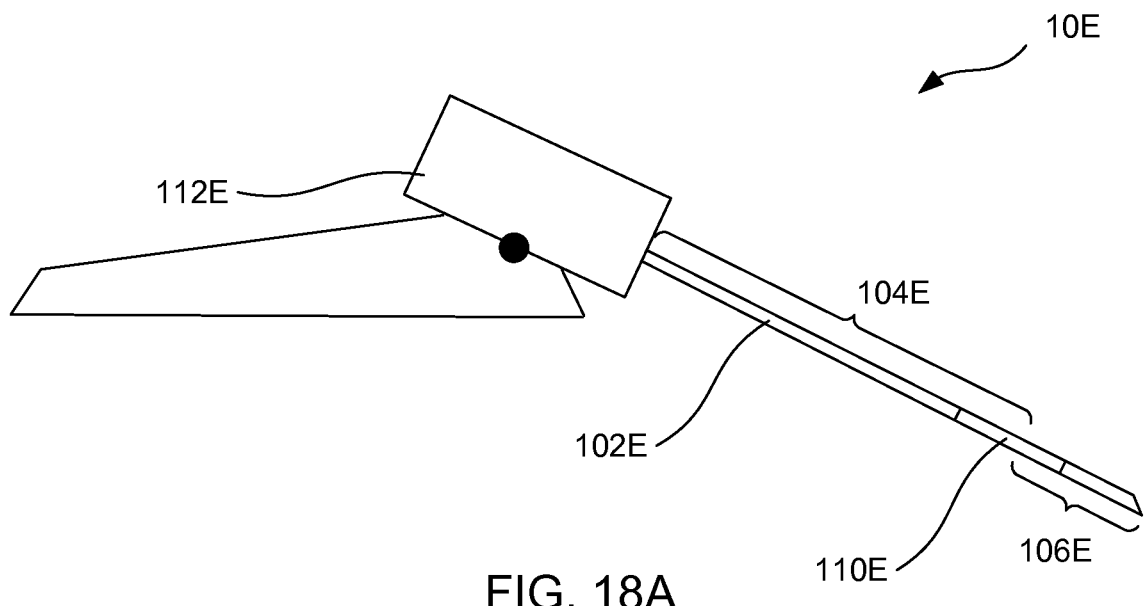
FIG. 18A is a side elevation view of an exemplary needle system including a straight section.
Figure 18B:
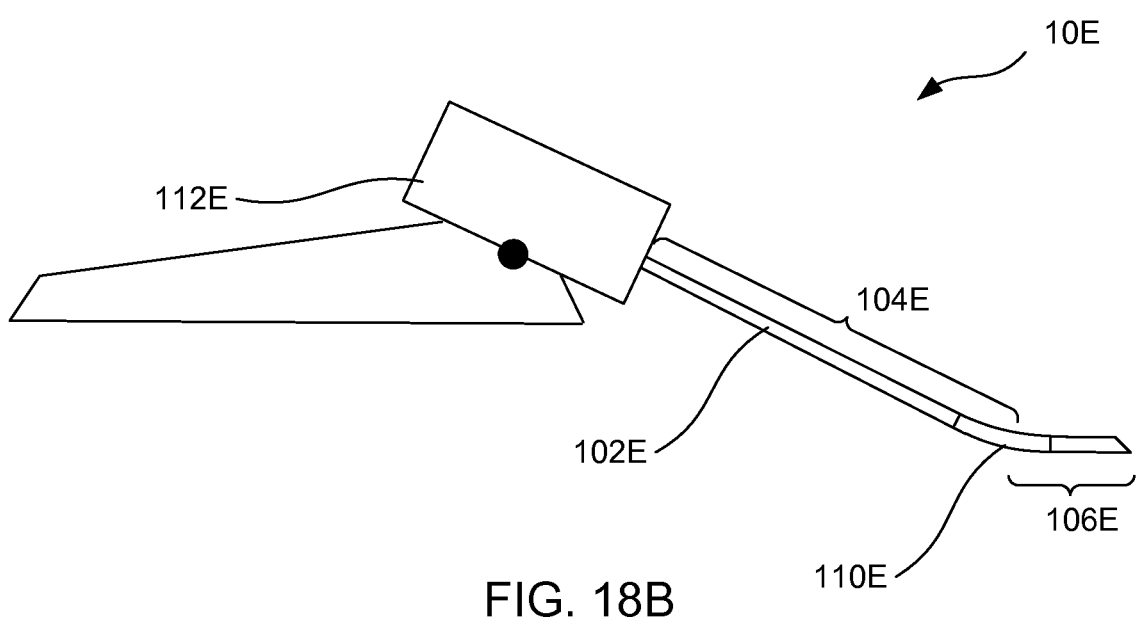
FIG. 18B is a side elevation view of an exemplary needle system including a bent section.

Referring to FIGS. 18A and 18B, an exemplary needle system 10E may include a needle 102E including a bent section 106E and a straight section 104E, which may be attached to a housing 112E. Bent section 106E and straight section 104E may be interposed by a bend 110E, which may include a shape memory material. Bend 110E may be adjustable between the generally straight configuration shown in FIG. 18A and the bent configuration shown in FIG. 18B by changing its temperature. In some exemplary embodiments, only one or more bends 110E may include shape-memory materials, and the some exemplary embodiments substantially all of needle 102E may be constructed of shape-memory materials. In some exemplary embodiments, portions including shape memory materials may be configured to change from a substantially straight configuration to a bent configuration. In some exemplary embodiments, portions including shape memory materials may be configured to change from a first bent configuration to a second bent configuration.

In some exemplary embodiments, a needle may include portions having different diameters. For example, referring to FIG. 1, an exemplary needle may include a bent section 106 having a greater diameter than a straight section 104. Some exemplary embodiments may include a bent section 106 having a smaller diameter than a straight section 104. In some exemplary embodiments, substantially the entire needle may have substantially a constant diameter. See, e.g., FIG. 6.

A method of using an exemplary needle system 10 may include selecting an appropriate needle system 10 based at least in part on at least one of the anticipated use of the needle system 10, desired needle gauge, angle 105, length of straight section 104, length of bent section 106, and/or the thickness 18 of the tissue 16 overlaying the structure to be accessed. The appropriate needle system 10 may aligned with a vein 12 such that housing 112 is generally perpendicular to the skin surface 14. The needle 102 may be urged into the tissue 16 overlaying the vein 12. This step may occur after applying a tourniquet to an appropriate spot on the patient's limb, for example, as would be known to those of ordinary skill. The bent section 106 may provide a depth stop and/or depth indication, such that the needle 102 has penetrated a known depth when the bend 110 reaches the skin surface 14. The bent section 106 of the needle 102 may be advanced substantially parallel to the vein 12. This step may be assisted by a concave groove or other feature extending longitudinally across a base 200 of the needle system 10. The needle 102 may be utilized to draw blood, inject pharmaceuticals, etc. In some circumstances the needle 102 may remain installed for an extended period of time, and in other circumstances the needle 102 may be withdrawn shortly after drawing blood, injecting pharmaceuticals, etc.

If the exemplary needle system 10 will be used to infuse fluids, appropriate infusion tubing may be coupled to the housing 112. If the exemplary needle system 10 will be used to obtain a blood sample, one or more blood sample tubes may be used to collect blood from the vein 12.

When an exemplary needle system 10 is no longer required, the needle 102 may be withdrawn from the vein 12. The base 200 may be pivoted into the safety guard position such that base 200 protects point 108. The needle system 10 may be discarded in an appropriate manner.

All patents, patent applications, and any other references identified in this disclosure are expressly incorporated by reference.

While exemplary embodiments have been set forth above for the purpose of disclosure, modifications of the disclosed embodiments as well as other embodiments thereof may occur to those skilled in the art. Accordingly, it is to be understood that the disclosure is not limited to the above precise embodiments and that changes may be made without departing from the scope. Likewise, it is to be understood that it is not necessary to meet any or all of the stated advantages or objects disclosed herein to fall within the scope of the disclosure, since inherent and/or unforeseen advantages may exist even though they may not have been explicitly discussed herein.

What is claimed is:

1. An access device comprising:
   a rigid non-linear guide configured to be inserted into a body structure; and
   a conduit having a first configuration for insertion into the body structure in which at least a portion of a length of the conduit is tightly collapsed and affixed to an exterior of at least a portion of a distal section of the guide, and a second configuration in which inner and outermost dimensions along the entire length of the conduit are expanded by the application of internal pressure to provide an expanded internal passage,
   wherein the guide is configured to be detachable and removable from the conduit after the conduit is in the expanded second configuration.

2. The access device of claim 1, further comprising an implant disposed around the conduit in a collapsed first configuration, wherein, when the conduit is expanded to the second configuration, the implant is deployed to be retained in the body structure in an expanded second configuration, and wherein the implant is configured to be retained in the body structure following the removal of the guide and the conduit from the body structure.

3. The access device of claim 1, wherein the access device is configured to be inserted into the body structure with a robotic mechanism.

4. The access device of claim 1, wherein the guide has a proximal section and a bend section, wherein the bend section is disposed between the distal section and the proximal section and is configured to retain the distal section at a fixed angle with respect to the proximal section.

5. The access device of claim 1, wherein the guide includes a first bend section, a center section, a second bend section, and a proximal section, wherein the first bend section is configured to retain the distal section at a fixed angle with respect to the center section, and wherein the second bend section is configured to retain the center section at a fixed angle with respect to the proximal section.

6. The access device of claim 5, wherein the distal section of the guide is retained substantially parallel to the proximal section of the guide.

7. The access device of claim 1, wherein the body structure is at least one of a vascular space, body lumen, or internal body tissue.

8. The access device of claim 1, wherein the conduit is configured to provide a passage for a vascular repair system.

9. The access device of claim 1, further comprising at least one sensor at a proximal end of the conduit, wherein the proximal end of the conduit is configured to couple to a monitoring system and to a supply arranged to provide at least one of air, water, sterile fluid, disinfectant, medications, therapeutic substances, or combinations thereof.

10. The access device of claim 1, wherein the conduit comprises multiple lumens.

11. The access device of claim 1, wherein the guide is at least one of a needle, wire, or stylet, and the conduit is at least one of a cannula, catheter, or trocar.

12. The access device of claim 1, wherein the conduit is affixed to the guide by heat shrinking.

13. The access device of claim 1, wherein the conduit is expandable to the second configuration by at least one of fluid pressure, mechanical pressure, instruments, or combinations thereof.

14. The access device of claim 1, wherein the conduit is configured to be selectively retained in its expanded configuration after detaching and removing the guide from the conduit.

15. An access device comprising:

a rigid non-linear penetrating guide; and a conduit, defining an internal passage, having a first configuration for insertion into a body structure in which at least a distal portion of a length of the conduit is tightly collapsed and affixed to an exterior of at least a portion of a distal section of the penetrating guide, and a second configuration in which the internal passage and outermost dimension along the entire length of the conduit are expanded from the first configuration by the application of internal pressure, wherein the penetrating guide is configured to be detachable and removable from the conduit after the conduit is in the expanded second configuration.

16. The access device of claim 15, wherein the access device is configured to be inserted into the body structure with a robotic mechanism.

17. The access device of claim 15, wherein the body structure is at least one of a vascular space, body lumen, or internal body tissue.

18. The access device of claim 15, wherein the conduit is configured to provide a passage for a vascular repair system.

19. The access device of claim 15, wherein the conduit comprises multiple lumens.

20. The access device of claim 15, wherein the conduit is expandable by at least one of fluid pressure, mechanical pressure, instruments, or combinations thereof.

21. The access device of claim 15, wherein the conduit is asymmetrically expandable to the irregular shape of devices, implants, or instruments passed through the conduit.

22. The access device of claim 14, wherein the conduit is configured to be selectively collapsed after detaching and removing the guide from the conduit.

* * * * *